United States Patent [19]
Myhres

[11] Patent Number: 5,759,180
[45] Date of Patent: Jun. 2, 1998

[54] OSTOMY BAG COVER AND ASSEMBLY

[76] Inventor: Donita F. Myhres, 20226—140th Pl. SE., Kent, Wash. 98042

[21] Appl. No.: 789,461

[22] Filed: Jan. 27, 1997

[51] Int. Cl.$^6$ ............................................. A61F 5/44
[52] U.S. Cl. ................................. 604/332; 428/343
[58] Field of Search .......................... 604/332, 338, 604/342, 345, 353, 349; 428/343

[56] References Cited

U.S. PATENT DOCUMENTS

| | | | |
|---|---|---|---|
| D. 245,119 | 7/1977 | Harris | D24/58 |
| D. 270,091 | 8/1983 | Setzer | D24/58 |
| 2,662,525 | 12/1953 | Priebe | 128/283 |
| 4,331,148 | 5/1982 | Steer et al. | 128/283 |
| 4,439,191 | 3/1984 | Hogan | 604/332 |
| 4,519,797 | 5/1985 | Hall | 604/332 |
| 4,526,280 | 7/1985 | Taylor | 215/100.5 |
| 4,543,097 | 9/1985 | Van Polen | 604/333 |
| 4,606,736 | 8/1986 | Van De Weghe | 604/322 |
| 4,623,338 | 11/1986 | Larson | 604/339 |
| 4,705,512 | 11/1987 | Faucher | 604/332 |
| 5,026,362 | 6/1991 | Willett | 604/345 |
| 5,074,851 | 12/1991 | Plass et al. | 604/333 |
| 5,135,519 | 8/1992 | Helmer | 604/332 |
| 5,178,614 | 1/1993 | McDowell et al. | 604/332 |
| 5,248,308 | 9/1993 | von Emster | 604/337 |
| 5,591,144 | 1/1997 | Smith | 604/332 |

Primary Examiner—Robert A. Clarke
Attorney, Agent, or Firm—Teresa J. Wiant; Glenn D. Bellamy

[57] ABSTRACT

The present invention provides a cover for an ostomy bag which is opaque to camouflage waste in the ostomy bag. The cover is also moisture resistant to prevent the deterioration of the cover when exposed to moisture as well as to prevent the cover from separating from an ostomy bag when exposed to moisture. The cover may also include decorative patterns.

12 Claims, 2 Drawing Sheets

OSTOMY BAG COVER AND ASSEMBLY

TECHNICAL FIELD

This invention relates to a cover for use on an ostomy bag. More particularly, this invention relates to an opaque, moisture resistant ostomy bag cover.

BACKGROUND OF THE INVENTION

An ostomy is an operation in which an artificial stoma or opening is surgically created. The opening itself is also referred to as an ostomy. Usually, ostomies are created through the abdominal wall to allow bodily wastes to be discharged when disease or injury has incapacitated the normal excretion channels. Ostomies may be created for different organs, such as the colon, large bowel, bladder or ureter. Generally, an external appliance or bag is attached to the ostomy to collect waste.

SUMMARY OF THE INVENTION

The present invention provides an ostomy bag cover comprising a body portion and a neck portion. The body portion is shaped to substantially cover a body portion of a front side of an ostomy bag. The neck portion is shaped to substantially cover at least a lower part of a neck portion of a front side of an ostomy bag. The ostomy bag cover is substantially opaque. The ostomy bag cover is also substantially moisture resistant. In addition, the ostomy bag cover is affixable to the front side of an ostomy bag.

The ostomy bag cover includes a front side and a rear side. In a preferred form of the invention, the rear side includes an adhesive material. The adhesive material may be pressure sensitive. It is preferred that the adhesive material is attachable, removable, and reattachable to an ostomy bag.

The front side of the ostomy bag cover may include a decorative design. The ostomy bag cover may be composed of vinyl.

The present invention also provides an ostomy bag and ostomy bag cover assembly. The ostomy bag includes a front side and a rear side. The ostomy bag includes a body portion and a neck portion. The ostomy bag cover is affixed over substantially all of the body portion on the front side of the ostomy bag and at least a part of the neck portion on the front side of the ostomy bag. The ostomy bag cover is substantially opaque and substantially resistant to separating from the ostomy bag when the ostomy bag and ostomy bag cover assembly is exposed to moisture.

In the assembly, the ostomy bag cover may include a front side and a rear side and the rear side of the ostomy bag cover may include an adhesive material. The adhesive material may be pressure sensitive. The adhesive material may also be detachable and placeable, and reattachable to the ostomy bag.

The front side of the ostomy bag cover may also include a decorative design. The ostomy bag cover may also be composed substantially of vinyl.

These and other advantages and features will become apparent from the detailed description of the best mode for carrying out the invention that follows.

BRIEF DESCRIPTION OF THE DRAWINGS

Like reference numerals are used to denote like parts throughout the several figures of the drawings, and.

BEST MODE FOR CARRYING OUT THE INVENTION

Figure 1:
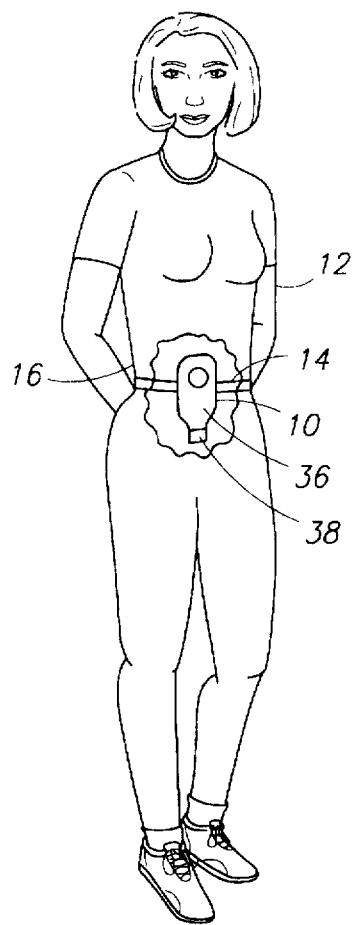
FIG. 1 shows a child wearing an ostomy bag.
Figure 2:
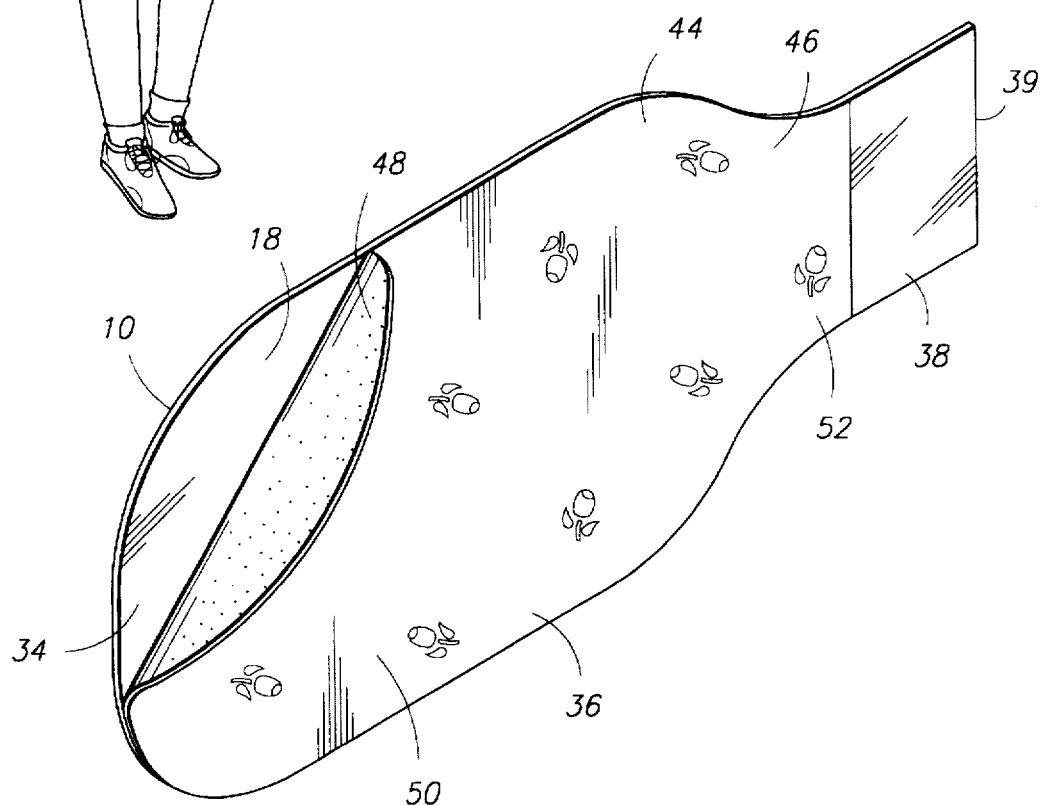
FIG. 2 is a pictorial view of an ostomy bag and an ostomy bag cover constructed according to the present invention, viewing the ostomy bag and cover from the front side of the ostomy bag.
Figure 3:
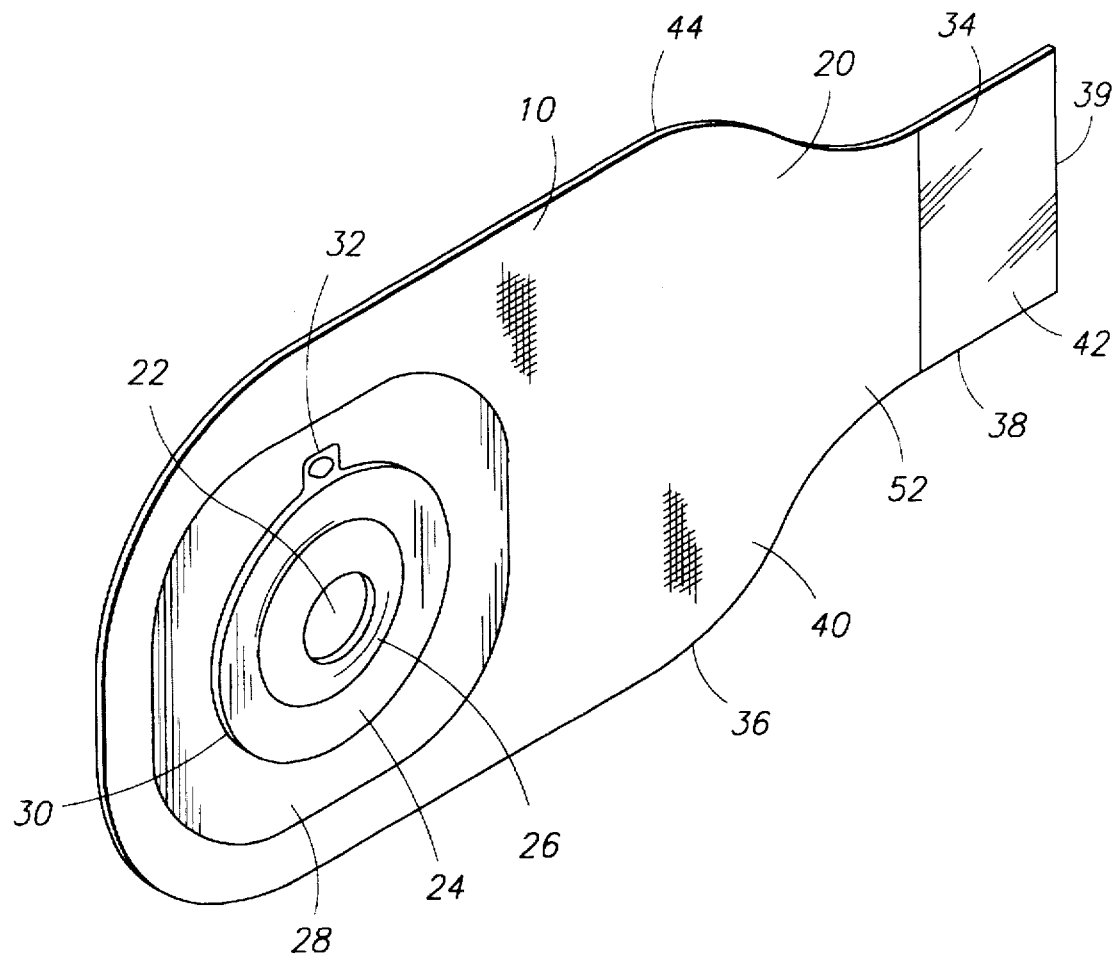
FIG. 3 is a pictorial view of the ostomy bag and cover shown in FIG. 2, viewing the ostomy bag from the rear.

Referring to FIGS. 1–3, an ostomy bag 10 is worn by a wearer 12 when an artificial stoma or ostomy has been surgically created. The ostomy bag 10 may be held in place by a belt 14 which wraps around the waist 16 of the wearer 12. The ostomy bag 10 comprises a front side 18 and a rear side 20. On the rear side 20 of the ostomy bag 10 is an opening 22 surrounded by an artificial stoma adhesive ring 24, an artificial stoma adhesive seal 26, a skin adhesive ring 28, and a substantially rigid ring 30 and tab 32. The tab 32 may be used to attach the ostomy bag 10 to the belt 14 which wraps around the waist 16 of the wearer 12.

The ostomy bag 10 is constructed of a flexible translucent material. The ostomy bag 10 has a body portion 36 and a narrower neck portion 38. On the rear side 20 of the ostomy bag 10, a breathable layer 40 covers the body portion 36 and part of the neck portion 38. This creates an end part of the neck 42 which is not covered with the breathable layer 40. The end part of the neck portion 38 may be folded and clamped or otherwise held closed to seal off the opening 39 in the neck portion 38 of the ostomy bag 10.

The present invention provides an ostomy bag cover 44 which is affixable to the front side 18 of the ostomy bag 10. The ostomy bag cover 44 includes a body portion 50 and a neck portion 52. The body portion 50 of the cover 44 is approximately the same size as the body portion 36 of the front side 18 of the ostomy bag 10. The neck portion 52 of the cover 44 is approximately the same size as the lower part of the neck portion 38 of the front side 18 of the ostomy bag 10. Thus, the cover 44 is sized to fit over or cover the body portion 36 of the front side 18 of the ostomy bag 10 and the lower part of the neck portion 38 of the front side 18 of the ostomy bag 10. However, it would be within the scope of the present invention for the cover 44 to include a neck portion 52 which covers substantially all of the neck portion 38 of the front side 18 of the ostomy bag 10. Additionally, the cover 44 may be sized and shaped to fit other types of ostomy bags.

According to the present invention, the cover 44 is made of a moisture resistant opaque material. The cover 44 has a front side 46 and a rear side 48. In a preferred form of the invention, the rear side 48 is covered with an adhesive material to allow the cover 44 to be affixed to the ostomy bag 10. An adhesive may be applied all over the rear side 48 of the cover 44, or alternatively, the adhesive may be applied at discrete locations on the rear side 48 of the cover. In a preferred form of the invention, the adhesive is releasable such that the cover may be removed from the ostomy bag and reattached by pressing the cover bag on to the ostomy bag 10. Also in a preferred form of the invention, the adhesive material is pressure sensitive such that it adheres the cover 44 to the ostomy bag 10 when pressed. It is contemplated that the cover 44 could be delivered with a protective sheet adhered to the adhesive material. The protective sheet could then be peeled from the cover 44 before the cover 44 is adhered to an ostomy bag.

It is preferred that the cover 44 be opaque such that waste in the ostomy bag 10 is not visible when the cover 44 is in place. In a preferred form of the invention, the front side 46 of the cover 44 is printable to allow a design or pattern to be applied to the cover. The pattern or design may be specific to the wearer, such as masculine designs for men, feminine designs for women, and juvenile designs for children. The decorative patterns or designs may be printed or otherwise affixed onto the cover by any method known in the art or later developed. Suitable known methods include applying a pattern to the cover by the use of a plotter type printer. The designs or patterns may be computer generated, free hand drawings, or photographs.

It is also preferred that the cover 44 be moisture resistant such that it will not deteriorate when exposed to moisture and that it will stay adhered to the ostomy bag 10 when exposed to moisture, such as in a shower or bath.

Suitable materials for making the ostomy bag cover 44 include contact paper and printable vinyl, such as Cast No. 52150 available from Fargo Electronics, Inc. or Calendared No. 52152 available from Fargo Electronics, Inc. Relatively thin vinyl or contact paper, such as 2 millimeter vinyl or contact paper, is suitable for use in the present invention. Other suitable materials could include waterproof or moisture resistant fabric, papers, or plastic films.

The present invention provides a ostomy cover 44 which overcomes many of the aesthetic problems associated with the use of an ostomy. The ostomy cover 44 is opaque to keep waste inside of the ostomy bag 10 out of sight of the wearer and other people assisting the wearer. In addition, the moisture resistant qualities of the cover 44 allow it to be worn during a bath or shower or at other times when the wearer may be in contact with water and would still like for the waste in the ostomy bag to be out of sight. Also, the cover 44 can provide decorative designs or patterns which may be especially important to children wearing an ostomy so that their cover 44 may make the ostomy bag 10 appliance a friendlier part of their life.

The present invention also provides an ostomy bag and ostomy bag cover assembly which provides an opaque cover to camouflage waste in the ostomy bag. The cover is like that described above. The cover may be replaced by removal of the cover from the bag. In addition, the cover may include decorative designs.

Although the preferred embodiments of the invention have been illustrated and described herein, it is intended to be understood by those skilled in the art that various modifications and omissions in form and detail may be made without departing from the spirit and scope of the invention as defined by the following claims.

What is claimed is:

1. An ostomy bag cover, comprising:
   a body portion shaped similarly to a body portion of a front side of an ostomy bag; and
   a neck portion shaped similarly to at least a lower part of a neck portion of a front side of an ostomy bag; said ostomy bag cover being substantially opaque, substantially moisture resistant, and affixable directly to the front side of said ostomy bag such that said body portion substantially covers said front side of an ostomy bag and said neck portion substantially covers at least a lower part of said neck portion of a front side of an ostomy bag.

2. An ostomy bag cover according to claim 1, wherein said ostomy bag cover includes a front side and a rear side and said rear side of said ostomy bag cover includes an adhesive material.

3. An ostomy bag cover according to claim 2, wherein said adhesive material is pressure sensitive.

4. An ostomy bag cover according to claim 2, wherein said adhesive material is attachable, removable, and reattachable to an ostomy bag.

5. An ostomy bag cover according to claim 1, wherein said ostomy bag cover includes a front side and a rear side and said front side of said ostomy bag cover includes a decorative design.

6. An ostomy bag cover according to claim 1 composed substantially of vinyl.

7. An ostomy bag and ostomy bag cover assembly wherein said ostomy bag includes a front side and a rear side and said front side includes a body portion and a neck portion, and said ostomy bag cover is affixed directly to substantially all of the body portion on the front side of the ostomy bag and at least a part of said neck portion of said front side, said ostomy bag cover being substantially opaque and substantially resistant to separating from said ostomy bag when said ostomy bag and ostomy bag cover assembly is exposed to moisture.

8. An ostomy bag and ostomy bag cover assembly according to claim 7, wherein said ostomy bag cover includes a front side and a rear side and said rear side of said ostomy bag cover includes an adhesive material.

9. An ostomy bag and ostomy bag cover assembly according to claim 7, wherein said adhesive material is pressure sensitive.

10. An ostomy bag and ostomy bag cover assembly according to claim 7, wherein said adhesive material is detachable and replaceable on said ostomy bag.

11. An ostomy bag and ostomy bag cover assembly according to claim 7, wherein said ostomy bag cover includes a front side and a rear side and said front side of said ostomy bag cover includes a decorative design.

12. An ostomy bag and ostomy bag cover assembly according to claim 7, wherein said ostomy bag cover is composed substantially of vinyl.

* * * * *